US008609366B2

(12) United States Patent
Bottlang et al.

(10) Patent No.: US 8,609,366 B2
(45) Date of Patent: Dec. 17, 2013

(54) METHOD AND SYSTEMS FOR TISSUE CULTURE

(75) Inventors: Michael Bottlang, Portland, OR (US); Mark B. Sommers, Beaverton, OR (US)

(73) Assignee: Legacy Emanuel Hospital & Health Center, Portland, OR (US)

( * ) Notice: Subject to any disclaimer, the term of this patent is extended or adjusted under 35 U.S.C. 154(b) by 1683 days.

(21) Appl. No.: 11/594,702

(22) Filed: Nov. 7, 2006

(65) Prior Publication Data

US 2008/0026419 A1     Jan. 31, 2008

Related U.S. Application Data

(60) Provisional application No. 60/834,280, filed on Jul. 28, 2006.

(51) Int. Cl.
*C12M 1/34*      (2006.01)
*C12M 3/00*      (2006.01)

(52) U.S. Cl.
USPC ............................. 435/40.5; 435/288.3; 435/4

(58) Field of Classification Search
None
See application file for complete search history.

(56) References Cited

U.S. PATENT DOCUMENTS 6,528,780 B1*   3/2003   Mitsuoka et al. ............. 250/216
7,198,908 B2*   4/2007   Ochi et al. ...................... 435/41

OTHER PUBLICATIONS

Leica Microsystems "DM LS2 and DM LB2" Leica Microsystems Brochure, May 17, 2004, 6 pages.*
Microbus "The microscope" <http://www.microscope-microscope.org/basic/microscope-parts.htm> archived Nov. 21, 2002 (accessed online Sep. 18, 2009), 2 pages.*
Imaging Technology Group (ITG) "Atomic Force Microscopy" <http://itg.beckman.illinois.edu/ms/equipment/microscopes/afm.htm>, 2005 (accessed online Sep. 18, 2009), 1 page.*
Mizuno, S. "A novel method for assessing effects of hydrostatic fluid pressure on intracellular calcium: a study with bovine articular chondrocytes" Am J Physiol Cell Physiol 2005, 288: pp. C329-C337.*
International Crystal Laboratories "Quick Press KBr Pellet Kit" ICL Catalog, Aug. 24, 2004, 2 pages.*
Guilak, F., C. Hung, and R. Vanderby, *Cell and tissue engineering*. J Biomech Eng, 2000. 122: p. 209.
Park, S., C.T. Hung, and G.A. Ateshian, *Mechanical response of bovine articular cartilage under dynamic unconfined compression loading at physiological stress levels*. Osteoarthritis Cartilage, 2004. 12(1): p. 65-73.
Huang, C.Y., et al., *Effects of cyclic compressive loading on chondrogenesis of rabbit bone-marrow derived mesenchymal stem cells*. Stem Cells, 2004. 22(3): p. 313-23.
Mauck, R.L., et al., *Functional tissue engineering of articular cartilage through dynamic loading of chondrocyte-seeded agarose gels*. J Biomech Eng, 2000. 122(3): p. 252-60.

(Continued)

*Primary Examiner* — Chris R Tate
*Assistant Examiner* — Aaron J Kosar
(74) *Attorney, Agent, or Firm* — Kolisch Hartwell, P.C.

(57) ABSTRACT

Systems and methods for providing dynamic mechanical loading and mechanical property assessment of tissue cultures in open dish cultures are provided. An actuator may be provided under a cell culture dish for driving the dish upward toward a fixed post member, thereby providing controlled compression of a tissue sample.

20 Claims, 7 Drawing Sheets

(56) References Cited

OTHER PUBLICATIONS

Demarteau, O., et al., *Dynamic compression of cartilage constructs engineered from expanded human articular chondrocytes.* Biochem Biophys Res Commun, 2003. 310(2): p. 580-8.

Hung, C.T., et al., *A paradigm for functional tissue engineering of articular cartilage via applied physiologic deformational loading.* Ann Biomed Eng, 2004. 32(1): p. 35-49.

Freed, L.E., et al., Joint resurfacing using allograft chondrocytes and synthetic biodegradable polymer scaffolds. J Biomed Mater Res, 1994. 28(8): p. 891-9.

Freed, L.E., G. Vunjak-Novakovic, and R. Langer, Cultivation of cell-polymer cartilage implants in bioreactors. J Cell Biochem, 1993. 51(3): p. 257-64.

Saini, S. and T.M. Wick, Concentric cylinder bioreactor for production of tissue engineered cartilage: effect of seeding density and hydrodynamic loading on construct development. Biotechnol Prog, 2003. 19(2): p. 510-21.

Hu, J.C. and K.A. Athanasiou, *Low-density cultures of bovine chondrocytes: effects of scaffold material and culture system.* Biomaterials, 2005. 26(14): p. 2001-12.

\* cited by examiner

METHOD AND SYSTEMS FOR TISSUE CULTURE

CROSS-REFERENCE TO RELATED APPLICATION

This application claims priority under 35 U.S.C. §119(e) to U.S. Provisional Patent Application Ser. No. 60/834,280 titled "Method and Device for Tissue Culture," filed Jul. 28, 2006. The complete disclosure of that application is hereby incorporated by reference for all purposes.

FIELD

The invention relates to apparatus and methods for dynamic mechanical loading and mechanical property assessment of tissue cultures.

BACKGROUND

Dynamic mechanical loading of engineered cartilage cells has been shown to improve mechanical properties of cells. Despite the fundamental importance of mechanical properties for the function of tissue-engineered cartilage, the ability to characterize and assess such mechanical properties in vitro lags far behind the sophistication of characterizing biological aspects of tissue development in response to mechano-stimulation. This may hinder systematic optimization of functional tissue engineering driven by mechanical function criteria, such as the expression of non-linear and viscoelastic behavior vital for the function of native articular cartilage.

Most existing systems for dynamic loading of tissue cultures in vitro (i.e., mechano-active bioreactors) do not enable measurement of tissue mechanical properties in vitro. Those tissue culture systems that do allow for assessment of some tissue mechanical properties in vitro apply loading in displacement control and not force control. Such loading in displacement control causes inherent limitations for assessment of tissue mechanical properties.

Conversely, systems for material testing of tissues under dynamic loading exist. However, these systems do not accommodate tissue cultures in culture dishes, and typically do not provide controlled loading and desired mechanical property assessment in the same apparatus. As such, they do not provide a practical culture environment typically required for cartilage tissue culture and experimentation.

SUMMARY

An apparatus provides dynamic mechanical loading and mechanical properties assessment of tissue cultures in open dish cultures. In a preferred embodiment a post is suspended over a tissue culture plate. An actuator controls movement of the post and plate relative to each other. A computer is programmed to control relative movement of the post and plate, and to process data assessing tissue mechanical properties of cell cultures contained in the plate.

DESCRIPTION

A cell culture system provides the capability of conducting controlled compression experiments on cells in cell culture dishes and related assessment of mechanical properties of the cells without transferring the cells to a different apparatus or environment. Preferred apparatus, as described below, and shown in the Figures, provides compression drive mechanisms below a set of cell dishes, thus avoiding contamination of the cell samples from the drive devices. Preferred systems and methods are described below. Numerous additional variations and modifications are enabled by the specification and covered by the claims below.

In a preferred configuration, an apparatus allows culturing of tissue in standard 35 mm diameter open-culture dishes, which is a routine and accepted setting for biological culture experiments. For specimen loading in compression, the culture dish can be driven upward against a static loading post which is fixed to a rigid support member, such as a cover. All drive components are situated in an enclosure beneath the culture dish(es). This arrangement, which seeks to minimize contamination risks, provides a robust culture environment required for long-term in vitro studies.

Compression under load control is driven by an electromagnetic actuator that transmits an upward directed force through a vertically-guided plunger to the culture dish. This electromagnetic actuator enables controlled application of dynamic loading, whereby the actuator force is proportional to the driving current signal. Resulting displacement may be recorded with a linear optical encoder which is connected to the vertical plunger for assessment of constitutive properties by means of load-displacement analysis. The applied load may be inferred from the signal supplied to the electromagnetic actuator. Alternatively, the induced load may be determined with a load cell or pressure sensor integrated in the loading post (for example, see FIG. 11). A software interface may be used to enable control of mechanical stimulation as well as evaluation of tissue mechanical properties, and changes which may occur during prolonged culture and stimulation periods.

In some applications, the cell culture apparatus may be sufficiently small to fit in a standard tissue culture incubator for long-term maintenance of tissue cultures in a controlled environment. In the incubator, the device enables application of controlled, cyclic mechanical deformation to one or more tissue cultures for mechanical stimulation of site cell samples. In addition, the device may be used to quantify mechanical properties of one or more tissue cultures, including, but not limited to, the elasticity modulus under static and dynamic loading conditions, the elastic and plastic components of said elasticity modulus and the shear modulus. Thus, the device may perform both mechanical stimulation and mechanical property evaluation by computed, controlled software interface.

Figure 1:
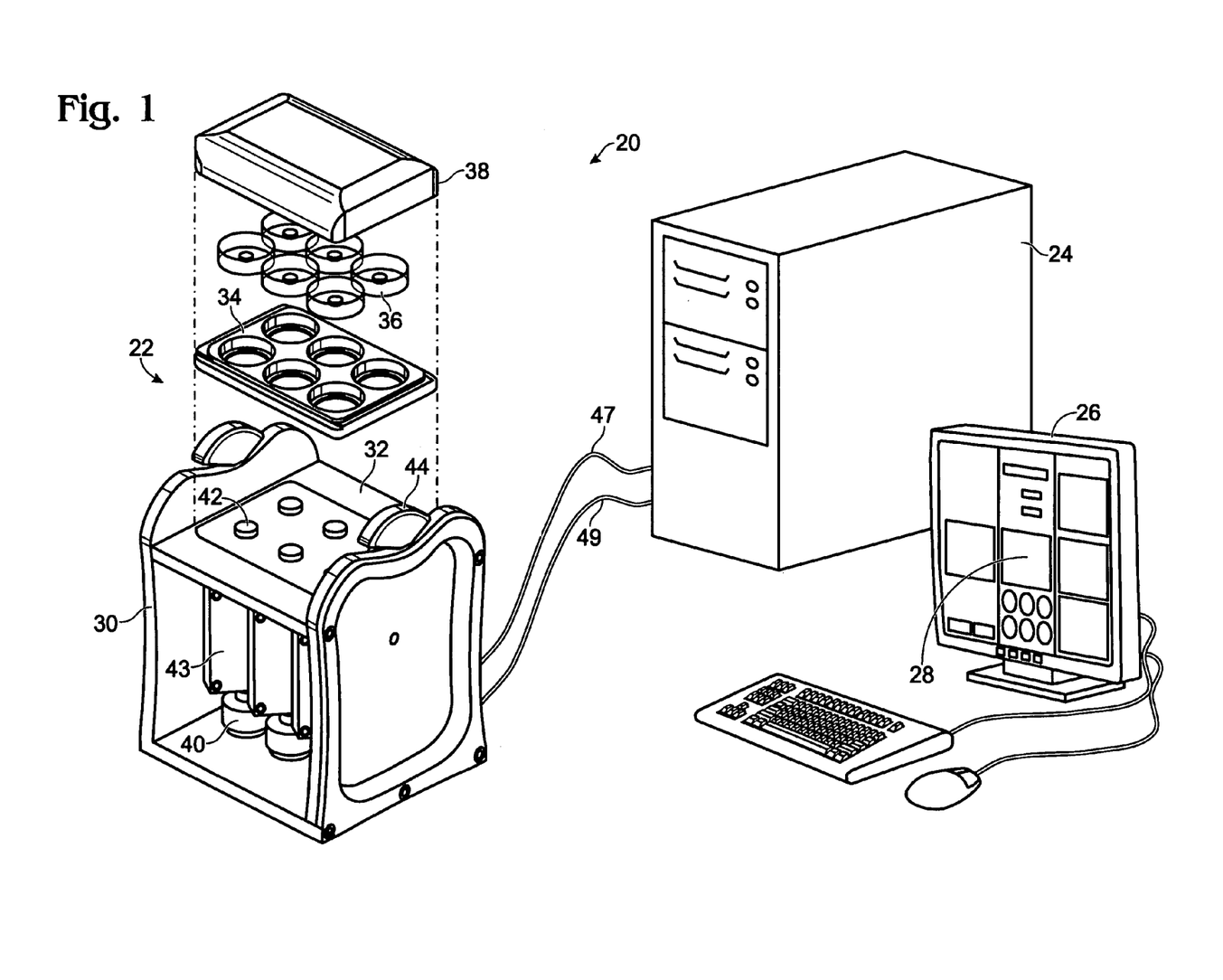
FIG. 1 is a perspective, partially-exploded view of a cell culture system.

System examples are illustrated in the figures. FIG. 1 shows cell culture system 20 including cell culture apparatus 22 connected to computer 24. Computer monitor 26 displays digital interface 28 for controlling compression experiments conducted on biological cell samples in cell culture apparatus 22 and reporting results. For example, the system shown in FIG. 1 is useful for conducting experiments on articular cartilage cells. Cell culture apparatus 22 includes a drive system housing 30. Housing 30 supports sample stage 32. Dish holder 34 is configured for placement on stage 32. Holes are provided in holder 34 for receiving cell culture dishes 36. Lid 38 is provided to fit on top of holder 34, thus containing and protecting cell cultures in dishes 36. Rigid housing 30 contains electromagnetic actuators 40 for driving plungers or pistons 42 upward to elevate respective dishes 36 toward stationary posts (not shown in FIG. 1) on the underside of lid 38. Displacement encoder 43 measures Z axis change of position of plunger 42. Latches 44 are provided for holding assembled holder 34 and lid 38 when positioned on stage 32.

The system shown in FIG. 1 depicts a six-dish device. However, the same principles may be applied to provide cell culture systems accommodating any number of cell culture dishes. The tray member or holder 34 ensures precise placement of six cell culture dishes or wells. Lid or cover 38 is compressed onto holder 34 by latches 44, in the closed position. Actuators 40 and displacement encoders 43 are positioned inside housing 30 underneath stage 32 and holder 34. Data cable 47 transmits the displacement sensor data to a controller in integrated computer 24. Second cable 49 supplies current, which induces force in the electromagnetic actuators. Software interface 28 is used to define mechanical stimulation signals for dynamic compression of tissue cultures, and to visualize results in material property measurements in tissue cultures, as shown in more detail in FIG. 12.

Figure 2:
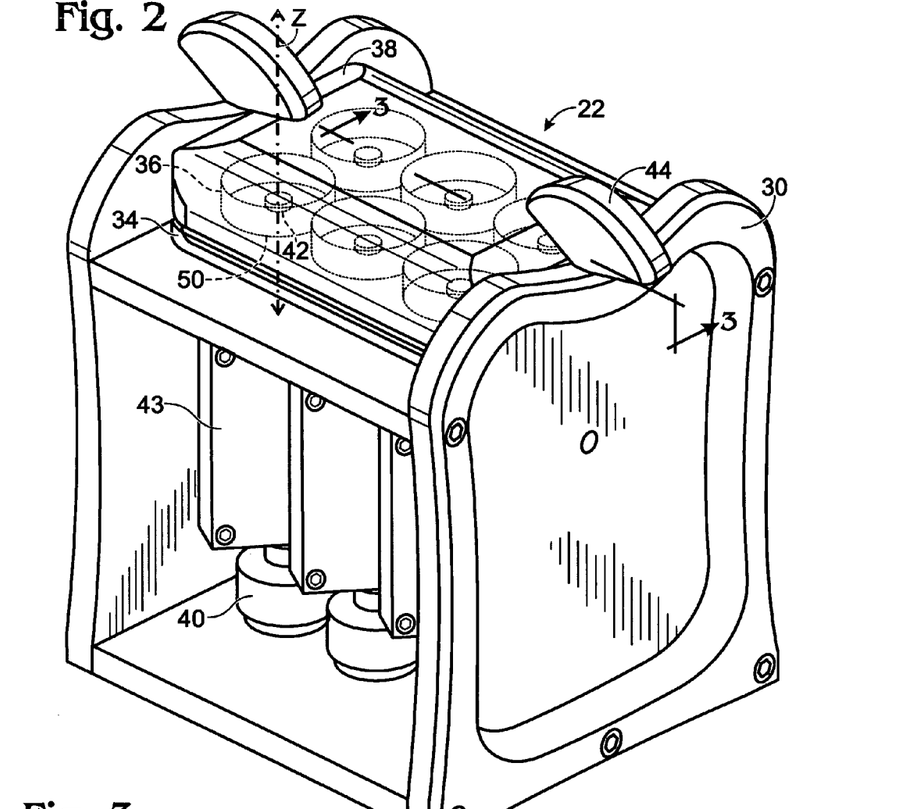
FIG. 2 is a perspective view of a cell culture apparatus.
Figure 3:
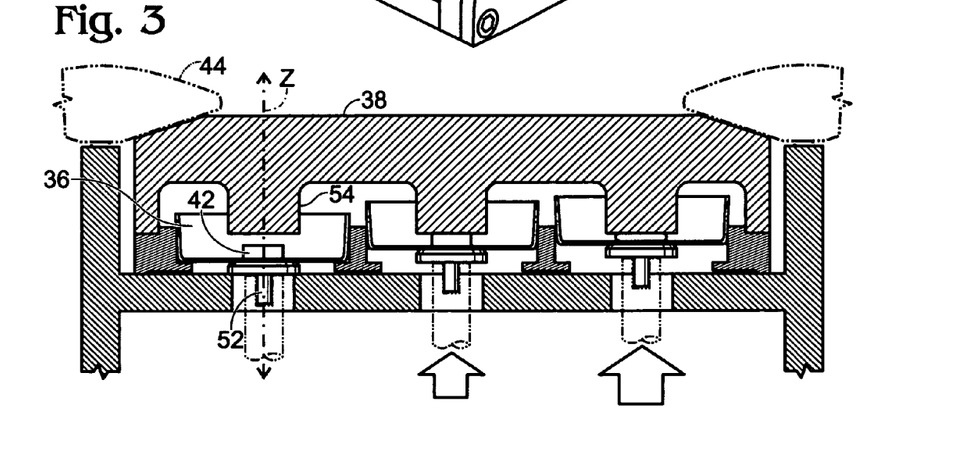
FIG. 3 is a partial, cross-sectional view of the cell culture apparatus shown in FIG. 2.
Figure 4:
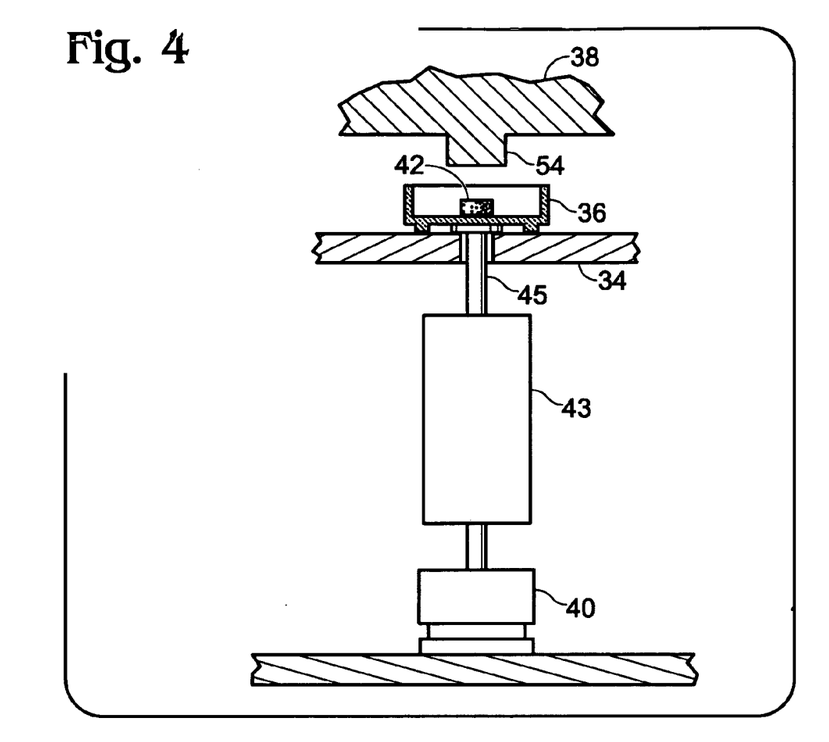
FIG. 4 is a partial, cross-sectional view, of an actuator device for compressing a cell sample in a cell culture apparatus.

FIG. 2 shows a perspective view of cell culture apparatus 22 with six cell culture plates 36 assembled into position in plate holder 34, covered by lid or cover 38. Cover 38 may be opaque, partially transparent, or totally transparent. Cover 38 may also be provided with viewing windows if desired. Electromagnetic actuator 40 is used to control the position of dish 36 along the Z axis, thereby compressing cell sample 42 against fixed posts on the underside of cover 38. The compression mechanism is shown in more detail in FIG. 3. A separate actuator is dedicated to each plate for driving plunger 52 to raise plate 36, and cell sample 42 into contact with post 54 on the underside of cover 38. Similarly, FIG. 4 shows actuator 40 positioned below dish holder 34 for controlling Z axis movement of plate 36.

Dynamic compression for mechanical stimulation of tissue samples will be carried out, preferably, by a separate electromagnetic actuator 43 for each dish. The actuator generates a linear force vector, which may be controlled by a computer-generated driving signal. Alternatively, electromechanical actuators may be employed to generate controlled linear displacement. It is generally preferable to use one actuator for each culture well. However, it is conceivable that a single actuator could be used to drive upward movement of more than one cell culture dish. Two or more actuators may be connected in parallel for simultaneous compression of two or more tissue cultures.

Displacement encoder 43 is provided for each culture dish for assessment of tissue culture compression in response to actuator force application. Encoder shaft 45 may serve as the piston which is driven by the actuator on one side, and which is acting on the culture dish 22 on the opposing side. Displacement sensing may be based on optical or inductive principals.

Figure 5:
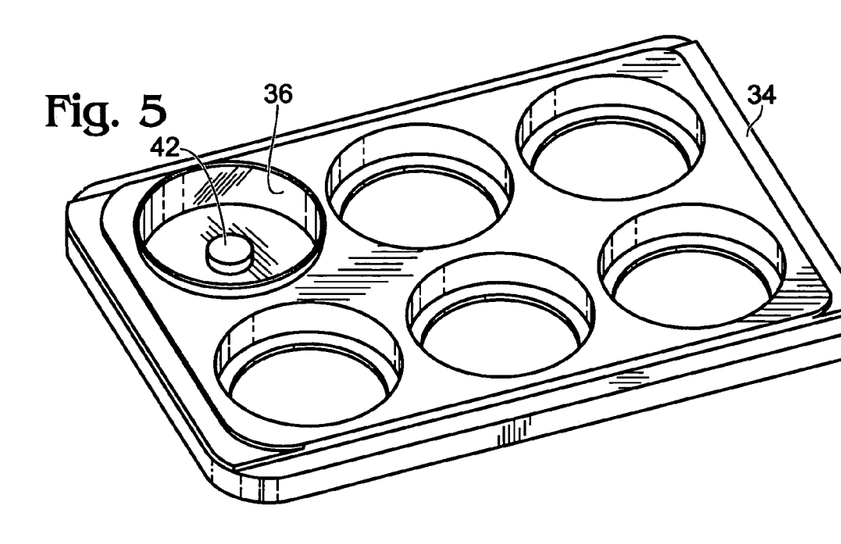
FIG. 5 is a perspective view of a holder for supporting cell culture plates or dishes.

FIG. 5 shows holder 34 supporting cell culture dish 36. Cell sample 42 is positioned approximately in the center of plate 36. Cell sample 42 is preferably supported in an appropriate matrix or scaffold.

Figure 6:
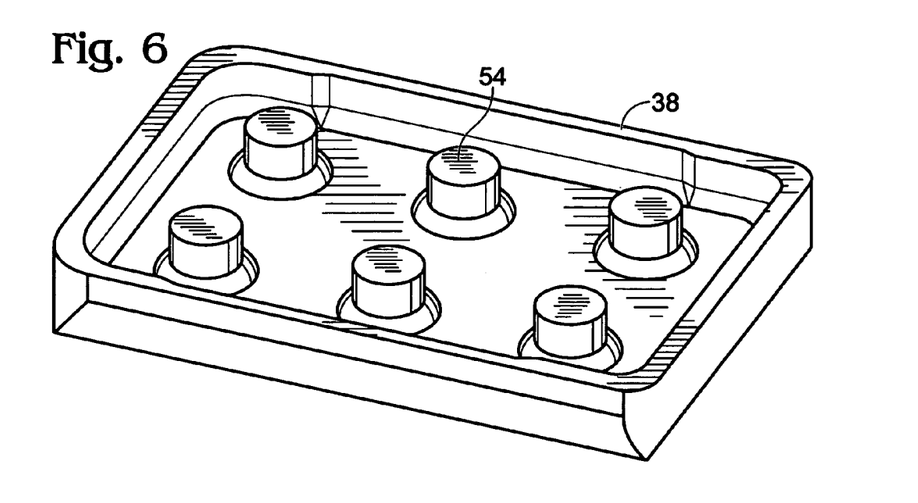
FIG. 6 is a perspective view of a lid with post members corresponding to dish positions in the holder shown in FIG. 5.
Figure 7:
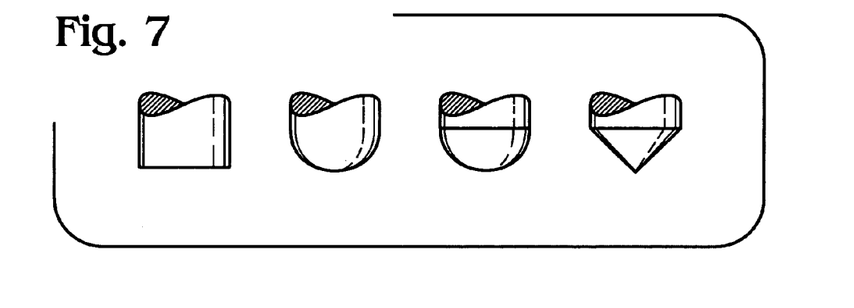
FIG. 7 shows partial side views of alternative configurations for the post members shown in FIG. 6.

FIG. 6 shows the underside of cover 38. Cylindrical posts 54 are provided for compressing cell samples, as described above. In FIG. 6, posts 54 have a substantially planar or flat surface. In this configuration, there are six posts arranged for precise positioning over six culture wells. The surface of each post end may be flat, as shown in FIG. 6, or may have other shapes, for example, as shown in FIG. 7, i.e., flat, cylindrical, spherical, conical, or other shapes, in order to achieve specific compression modes. One or more of the posts may be adjustable in height or length to accommodate tissue cultures of varying thickness. One or more of the posts may be equipped with a sensor for assessing force or pressure delivered to the tissue culture via the actuator and plunger below the dish. Other characteristics of the post may be varied such as coating composition, texturing, temperature control, etc.

Figure 8:
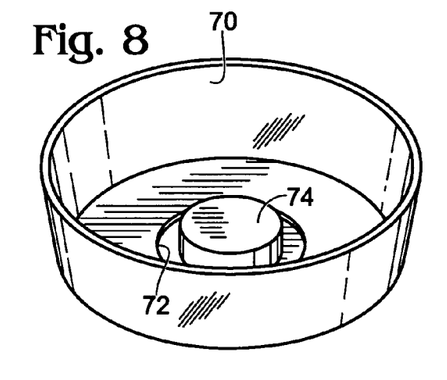
FIGS. 8 and 9 are perspective views of alternative cell culture dish designs.
Figure 9:
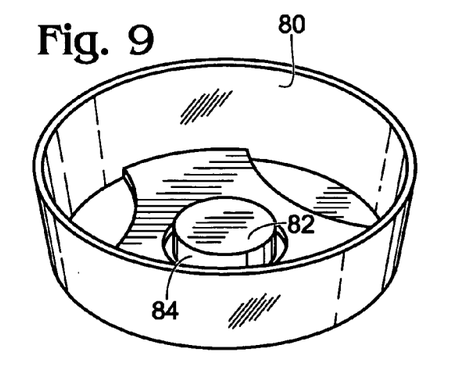

FIGS. 8 and 9 show different plate configurations with recesses for restricting location of cell sample disks in central areas corresponding to posts on the underside of the cover. In FIG. 8, dish 70 has recess 72 for receiving cell sample disk 74. In FIG. 9, dish 80 has insert 82 for defining a central recess for receiving cell sample disk 84. Insert 82 may be made of polystyrene, glass, stainless steel, or other bioinert materials used for tissue culture. If multiple culture dishes are used simultaneously, a tray member or holder may be used to facilitate handling and relative positioning between dishes.

Figure 10:
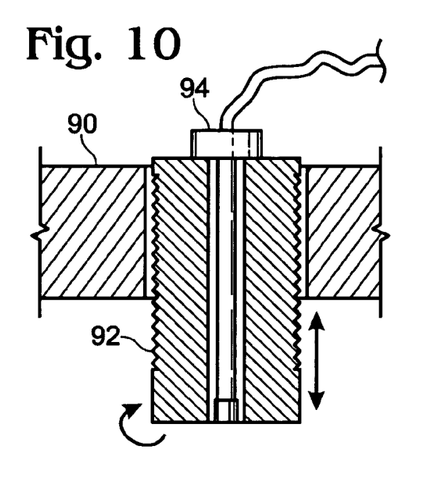
FIGS. 10 and 11 are partial side views of alternative post member design devices.
Figure 11:
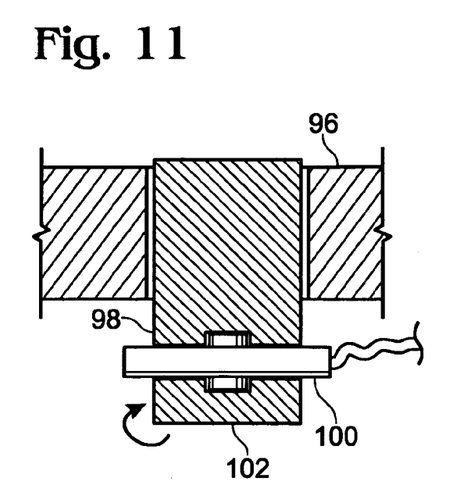

FIGS. 10 and 11 show optional devices for upper posts. In FIG. 10, cover 90 has adjustable posts 92. Pressure sensor 94 measures the pressure at the compression interface between the cell sample and the post surface. In FIG. 11, cover 96 includes posts 98 equipped with sensor 100 to detect forces applied to surface 102 of post 98.

Figure 12:
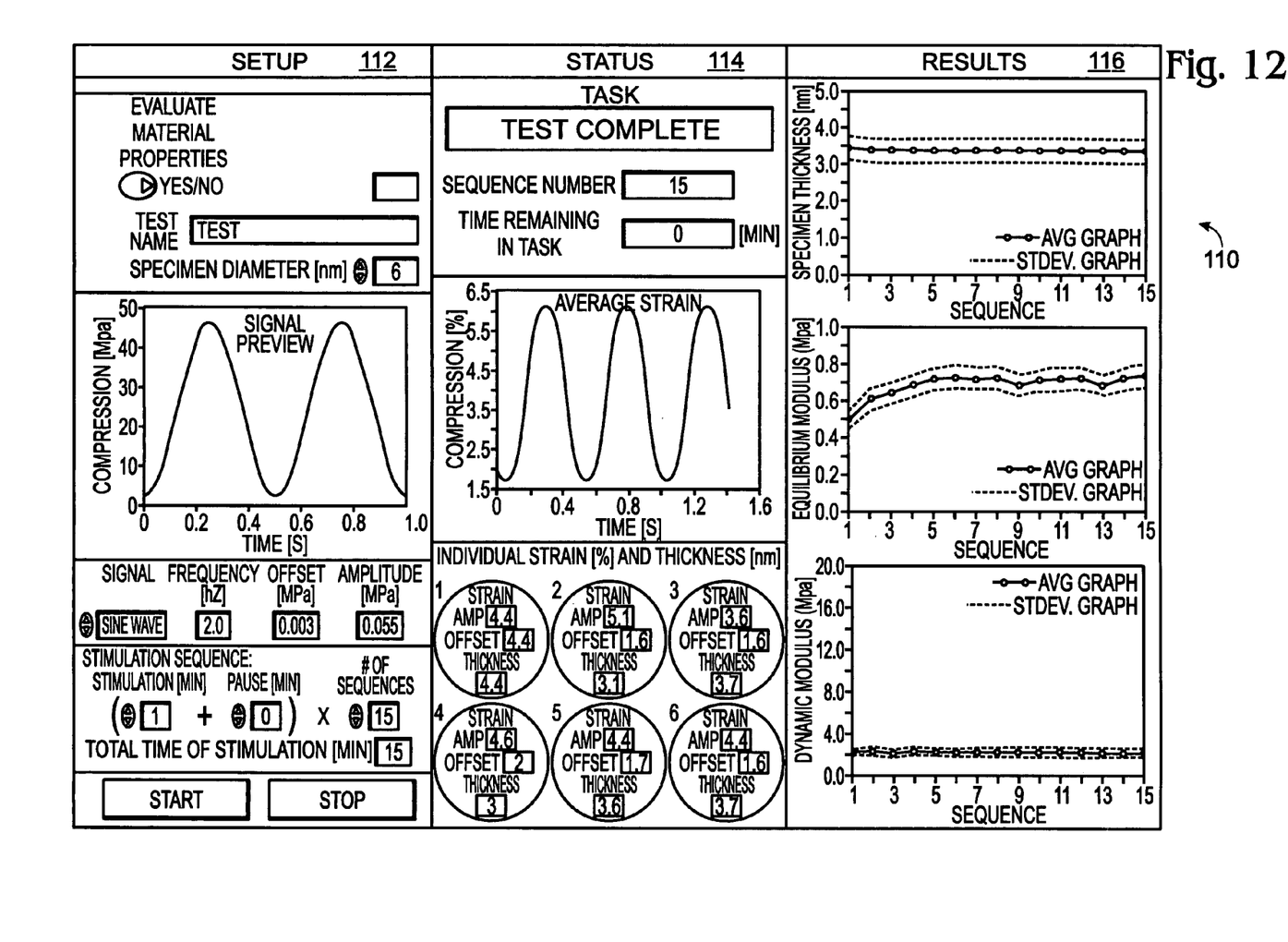
FIG. 12 is a front view of a display screen interface for controlling stress versus strain experiments, and reporting results.

FIG. 12 shows an example of a computer display interface for use in controlling and monitoring experiments conducted with a cell culture system, as described above. Display 110 is divided into three parts, set up area 112, status area 114, and results area 116. As shown in set up area 112, the operator may specify, among other things, specimen diameter, compression frequency, offset, amplitude, number of sequences, and total time of stimulation. Start and stop buttons may also be provided in the set up area. Status area 114 may show progression through a given experiment, average strain as a function of compression, as well as strain data for individual cell samples corresponding to the six plate positions in the culture apparatus. Results area 116 of display 110 may show graphical representations of cell sample thickness, equilibrium modulus, and dynamic modulus, among other data computations from completed experiments.

The system controller may be programmed to protect samples from excess strain (i.e., the compressive strain remaining whenever the dynamic, sinusoidal loading is at its minimum). If the strain is greater than a user-defined threshold (e.g. 30%), the system will halt mechano-stimulation to protect specimens from excessive strain.

Research has shown that dynamic compression facilitates matrix elaboration, while static compression does the opposite. During dynamic stimulation, specimens not only experience dynamic compression, but typically an increased amount of static offset compression due to creep as a consequence of prolonged dynamic loading. This will cause a continuous increase in the peak compressive strain during prolonged dynamic stimulation at a constant force amplitude. Thus, it may be beneficial to dynamically stimulate tissue only for a short period (minutes to an hour) so as not to exceed a certain strain value. After a pause, during which the tissue may relax to its original thickness, dynamic stimulation is then repeated. Accordingly, the program may provide the option for the operator to indicate a strain threshold, at which the system automatically adjusts or stops the loading magnitude for a given period of time in order to protect specimens from excessive strain.

EXAMPLE

An exemplary prototype cell culture system may be fabricated and evaluated as follows. With this prototype, first the inherent system performance on cartilage tissue was determined. Subsequently, the system's ability to quantify differences in material properties between cartilage tissue and a hydrogel tissue, which is typically used in tissue engineering applications, was measured.

For three hyaline cartilage explants, the dynamic load range of the prototype system was characterized. First, the load amplitude in response to a peak driving current of 1 A under sinusoidal loading frequencies of 0.1 Hz, 1 Hz, and 10 Hz, were evaluated, which resulted in peak compressive forces of 10.24 N, 10.36 N, and 10.18 N, respectively. These results demonstrated that the prototype system can reliably deliver sinusoidal dynamic loading profiles up to 10 Hz ((a) in FIG. 13).

Next, non-linear and viscoelastic constitutive properties were quantified to assess the system's ability to capture tissue material behavior. For characterization of non-linear elastic behavior, both the equilibrium compressive (Young's) modulus $M_E$ and the maximal dynamic modulus $M_{D,MAX}$ were quantified. $M_E$ was derived from the compressive strain in response to a static load of 1 N, applied for 30 minutes. The dynamic modulus $M_{D,MAX}$ was obtained under 10 Hz sinusoidal loading to a physiological contact stress (1.2 MPa). $M_{D,MAX}$ was extracted as the maximal slope $\delta\sigma/\delta\epsilon$ of the stress-strain curve ((b) in FIG. 13). Viscoelastic behavior was quantified in terms of the phase angle $\delta$ which correlates to the hysteresis between the loading and unloading pathways of the $\sigma/\epsilon$ curve. The prototype was able to quantify highly nonlinear constitutive behavior of native articular cartilage, whereby the equilibrium modulus ($M_E$=0.65±0.11 MPa) was over 15 times smaller than the 1 Hz dynamic modulus ($M_{D,MAX}$=15.7±0.9 MPa) ((c) in FIG. 13). Furthermore, it captured viscoelastic behavior in terms of the phase angle $\delta$=15.3°±6.2°.

For hydrogel specimens, $M_E$, $M_{D,MAX}$, and $\delta$ were quantified to demonstrate the ability of the prototype to capture differences between material of hydrogel and native cartilage specimens. Even in these relatively soft hydrogel tissues, the prototype system provided a highly sensitive assessment of dynamic material response, whereby consecutive tracings of stress-strain curves were virtually indistinguishable ((c) in FIG. 13). The equilibrium modulus of hydrogel ($M_E$=0.15±0.01 MPa) was over four times lower than that of the native cartilage (FIG. 2d). However, the dynamic modulus ($M_{D,MAX}$=0.26±0.01 MPa) was over 60 times lower than that of native cartilage. The phase angle of hydrogel ($\delta$=5.3±0.7°) yielded inferior viscoelasticity as compared to native cartilage.

In summary, the prototype system was able to quantitatively delineate constitutive material properties of both, articular cartilage and hydrogel. It furthermore quantified pronounced difference in non-linear and viscoelastic properties of cartilage and hydrogel. Consequently, the prototype cell culture system can assess material properties in vitro, and it simultaneously delivers well-defined mechano-stimulation over a wide range of loading parameters.

Figure 13:
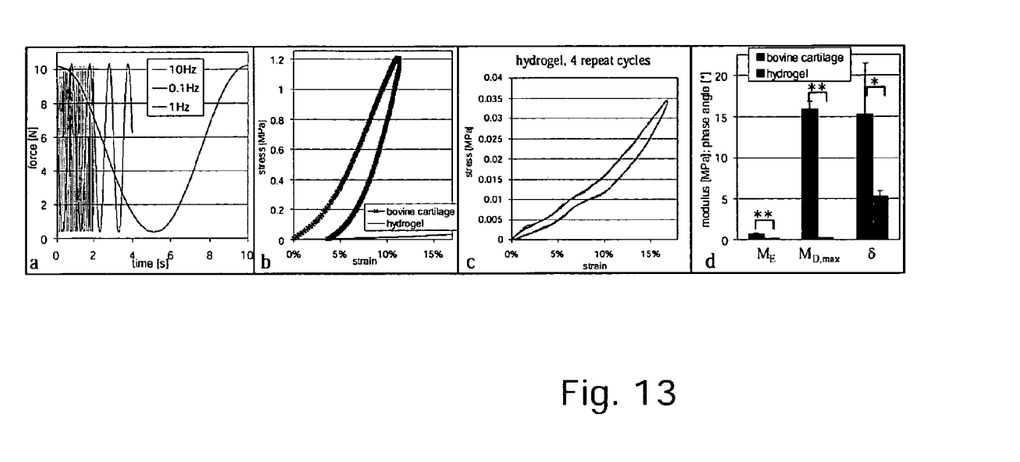
FIG. 13 shows graphical results of experiments conducted with a cell culture system as described below.

FIG. 13 shows graphs illustrating experimental results obtained with the cell culture system, as described above. In graph (a), the actuator retains load amplitude up to 10 Hz. In graph (b), stress-strain response at 1 Hz dynamic loading, demonstrates that cartilage has a higher dynamic modulus than hydrogel. In graph (c), the prototype system sensitively captured the stress-strain response of hydrogel, shown for four successive load cycles. In graph (d), the system quantitated significant material differences between cartilage and hydrogel (*$p<0.05$; **$p<0.001$).

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure.

Basic principles and concepts of the systems and methods described above may be summarized as follows. A tissue culture device and method for mechanical stimulation by dynamic compression and for material property evaluation may include one or more culture dishes, one or more post members suspended over the culture dishes, one or more actuators for compression of the culture dishes and cultures against the post members, and one or more displacement encoders for assessment of compression of the cultures in response to the applied compressive force. The device needs to be sufficiently small to fit into a standard tissue culture incubator. But the device enables application of controlled, cyclic mechanical deformation to one or more tissue cultures for mechanical stimulation of the cultures. The device may be capable of quantifying mechanical properties of one or more tissue cultures, including but not limited to the elasticity modulus under static and dynamic loading conditions, the elastic and plastic components of said elasticity modulus, and the shear modulus.

The device may provide mechanical stimulation and mechanical property evaluation in parallel or sequentially by a computer-controlled software interface. The culture dishes may be made of polystyrene, glass, or bioinert materials used for tissue culture vessels. The culture dish may have a recessed area which confines the tissue culture location to a central area. Alternatively, an insert may be used in standard culture dishes for confining the tissue location to a central area. The insert may be made of polystyrene, glass, stainless steel, or other bioinert materials used for tissue culture. Multiple dishes may be arranged in a tray member for handling.

One or more posts may be adjustable in height or length for accommodating tissue specimens of varying thickness. The surface of each post end for compression against tissue specimens may be flat, cylindrical, spherical, conical, or some other shape, in order to achieve specific compression modes. One or more posts may be instrumented with a sensor for assessment of force or pressure delivered to the tissue specimen. One or more posts may be integrated into a lid member for precise positioning over the culture dish(es). Actuators may be electromagnetic for provision of a controlled compression force. Actuators may be electromechanical for provision of a controlled compression displacement. Two or more actuators may be connected in parallel for parallel compression for two or more tissue cultures. The encoder shaft may serve as the piston which is driven by the actuator on one side and which is acting on the culture dish on the opposing side. Displacement sensing may be based on optical or inductive principles. Mechanical stimulation and mechanical property assessment of tissue cultures in culture dishes may be accomplished in one device. Mechanical stimulation and mechanical property assessment of tissue cultures in culture dishes may be accomplished in sequence over prolonged culture durations.

The following references are herein incorporated by reference in their entireties:

1. Guilak, F., C. Hung, and R. Vanderby, *Cell and tissue engineering*. J Biomech Eng, 2000.122: p. 209.
2. Park, S., C. T. Hung, and G. A. Ateshian, *Mechanical response of bovine articular cartilage under dynamic unconfined compression loading at physiological stress levels*. Osteoarthritis Cartilage, 2004.12(1): p. 65-73.
3. Huang, C. Y., et al., *Effects of cyclic compressive loading on chondrogenesis of rabbit bone-marrow derived mesenchymal stem cells*. Stem Cells, 2004. 22(3): p. 313-23.
4. Mauck, R. L., et al., *Functional tissue engineering of articular cartilage through dynamic loading of chondrocyte-seeded agarose gels*. J Biomech Eng, 2000. 122(3): p. 252-60.
5. Steinmeyer, J., *A computer-controlled mechanical culture system for biological testing of articular cartilage explants*. J Biomech, 1997. 30(8): p. 841-5.
6. Demarteau, O., et al., *Dynamic compression of cartilage constructs engineered from expanded human articular chondrocytes*. Biochem Biophys Res Commun, 2003. 310 (2): p. 580-8.
7. Hung, C. T., et al., *A paradigm for functional tissue engineering of articular cartilage via applied physiologic deformational loading*. Ann Biomed Eng, 2004. 32(1): p. 35-49.
8. Carver, S. E. and C. A. Heath, *Influence of intermittent pressure, fluid flow, and mixing on the regenerative properties of articular chondrocytes*. Biotechnol Bioeng, 1999. 65(3): p. 274-81.
9. Carver, S. E. and C. A. Heath, *Semi-continuous perfusion system for delivering intermittent physiological pressure to regenerating cartilage*. Tissue Eng, 1999. 5(1): P. 1-11.
10. Freed, L. E., et al., *Joint resurfacing using allograft chondrocytes and synthetic biodegradable polymer scaffolds*. J Biomed Mater Res, 1994. 28(8): p. 891-9.
11. Freed, L. E., G. Vunjak-Novakovic, and R. Langer, *Cultivation of cell-polymer cartilage implants in bioreactors*. J Cell Biochem, 1993. 51(3): p. 257-64.
12. Saini, S. and T. M. Wick, *Concentric cylinder bioreactor for production of tissue engineered cartilage: effect of seeding density and hydrodynamic loading on construct development*. Biotechnol Prog, 2003.19(2): p. 510-21.
13. Saini, S. and T. M. Wick, *Effect of low oxygen tension on tissue-engineered cartilage construct development in the concentric cylinder bioreactor*. Tissue Eng, 2004.10(5-6): p. 825-32.
14. Hu, J. C. and K. A. Athanasiou, *Low-density cultures of bovine chondrocytes: effects of scaffold material and culture system*. Biomaterials, 2005. 26(14): p. 2001-12.

We claim:

1. An apparatus for carrying out a compression experiment on a sample of biological cells in a cell culture plate, comprising:
   a holder configured for supporting a cell culture plate,
   a post member having a contact surface fixed along a vertical axis suspended above over the holder, and
   a compression device including a force-controlled electromagnetic actuator, and
   a plunger, configured to apply dynamic compression forces to a cell sample by driving the plunger and plate upward along the vertical axis toward the contact surface of the post member.

2. The apparatus of claim 1 further comprising
   a computer programmed to control force and frequency of compression forces applied to the cell sample.

3. The apparatus of claim 2, wherein the computer is also programmed to assess mechanical properties of the cell sample.

4. The apparatus of claim 1, wherein the compression force is proportional to the driving current signal applied to the actuator.

5. The apparatus of claim 1, further comprising a displacement encoder for determining the relative thickness of the cell sample corresponding to a given compression force.

6. The apparatus of claim 1, wherein the contact surface is substantially planar.

7. The apparatus of claim 1, wherein the contact surface is curved in a hemi-spherical or hemi-cylindrical shape.

8. The apparatus of claim 1, wherein the contact surface is tapered to a point.

9. The apparatus of claim 1, wherein the contact surface is textured.

10. The apparatus of claim 1, wherein the contact surface is substantially smooth.

11. An apparatus for carrying out a compression experiment on a sample of biological cells in a cell culture plate, comprising
    a holder configured for supporting a cell culture plate,
    a post member having a contact surface suspended over the holder along a vertical axis,
    a force-controlled compression device configured to apply dynamic compression forces to a cell sample by driving the plate or the post member along the vertical axis,
    a displacement encoder configured to assess the extent of sample compression as a function of compressive force, and
    a computer connected to the force-controlled compression device;
    wherein the contact surface of the post member is adjustable along the vertical axis and wherein the computer is programmed to control force and frequency of compression forces applied to the cell sample.

12. The apparatus of claim 11, wherein the compression device is configured to drive the post member toward the cell culture plate, the cell culture plate remaining fixed along the vertical axis.

13. The apparatus of claim 11 further comprising a computer programmed to control force and frequency of compression forces applied to the cell sample.

14. The apparatus of claim 11, wherein the computer is also programmed to assess mechanical properties of the cell sample.

15. The apparatus of claim 11, wherein the computer is programmed to control compression loading via the compression device, including a test phase and a stress versus strain evaluation phase.

16. The apparatus of claim 11, wherein the compression device includes a plunger and a force-controlled electromagnetic actuator for driving the plunger under the plate.

17. The apparatus of claim 16, wherein the compression force is proportional to the driving current signal applied to the actuator.

18. An apparatus for carrying out a compression experiment on a sample of biological cells in a cell culture plate, comprising
a holder configured for supporting the cell culture plate,
a post member having a contact surface fixed along a vertical axis, the post member being suspended over the holder,
a force-controlled electromagnetic actuator located below the holder, the actuator being configured to drive a cell sample contained in the cell culture plate along the vertical axis into contact with the contact surface of the post member,
a sensing device for determining an amount of force exerted on the cell sample,
a displacement encoder configured to determine a relative thickness of the cell sample corresponding to a particular compressive force measured by the sensing device, and
a computer programmed to control force and frequency of compressive forces exerted on the cell sample, and to assess mechanical properties of the cell sample based on force and displacement data.

19. The apparatus of claim 18 further comprising
a sensing device for determining the amount of force exerted on the cell sample, the displacement encoder being configured to determine a relative thickness of the cell sample corresponding to a particular compressive force measured by the sensing device.

20. An apparatus for carrying out a compression experiment on a sample of biological cells in a cell culture plate, comprising
a holder configured for supporting the cell culture plate,
a post member having a contact surface fixed along a vertical axis, the post member being suspended over the holder,
a force-controlled electromagnetic actuator located below the holder, the actuator being configured to drive a cell sample contained in the cell culture plate along the vertical axis into contact with the contact surface of the post member,
a displacement encoder configured to determine a relative thickness of the cell sample, and
a computer programmed to control force and frequency of compressive forces exerted on the cell sample, and to assess mechanical properties of the cell sample based on force and displacement data.

* * * * *